(12) United States Patent
Itagaki et al.

(10) Patent No.: US 7,893,294 B2
(45) Date of Patent: Feb. 22, 2011

(54) PROCESS FOR PRODUCTION OF TRANS-2, 2-DIMETHYL-3-FORMYLCYCLOPROPANE-CARBOXYLIC ACID ESTER

(75) Inventors: Makoto Itagaki, Katano (JP); Ryo Minamida, Kyotanabe (JP); Kouji Yoshikawa, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 27 days.

(21) Appl. No.: 12/375,684

(22) PCT Filed: Aug. 13, 2007

(86) PCT No.: PCT/JP2007/066068

§ 371 (c)(1),
(2), (4) Date: Apr. 2, 2009

(87) PCT Pub. No.: WO2008/020639

PCT Pub. Date: Feb. 21, 2008

(65) Prior Publication Data

US 2009/0314987 A1   Dec. 24, 2009

(30) Foreign Application Priority Data

Aug. 18, 2006   (JP) .............................. 2006-223036

(51) Int. Cl.
  *C07C 69/74* (2006.01)
(52) U.S. Cl. ..................................... 560/124
(58) Field of Classification Search .................. 560/124
  See application file for complete search history.

(56) References Cited

U.S. PATENT DOCUMENTS 3,723,469 A  *  3/1973  Martel ..................... 260/343.3

2005/0240050 A1 * 10/2005 Minamida et al. .......... 560/124

FOREIGN PATENT DOCUMENTS

| EP | 1 783 130 A1 | 5/2007 |
| EP | 1 970 369 A1 | 9/2008 |
| JP | 2006-45194 A | 2/2006 |
| WO | WO 2007069759 | * 6/2007 |

OTHER PUBLICATIONS

Tetrahedron, (2001), vol. 57, No. 28, pp. 6083-6088.
L. Crombie et al., "Syntheses of 14C-Labelled (+)-trans-Chrysanthemum Mono- and Di-carboxylic Acids, and of Related Compounds", J. Chem. Soc. (C), 1970, pp. 1076-1080.

* cited by examiner

*Primary Examiner*—Nizal S Chandrakumar
(74) *Attorney, Agent, or Firm*—Sughrue Mion, PLLC

(57) ABSTRACT

A process for production of a trans-2,2-dimethyl-3-formyl-cyclopropanecarboxylic acid ester comprising:
  (A) a step of obtaining a mixture containing a trans-2,2-dimethyl-3-(hydroxymethyl)cyclopropanecarboxylic acid ester,
  (B) a step of conducting an oxidation treatment of the mixture obtained in the step (A) to obtain a mixture containing a crude trans-2,2-dimethyl-3-formylcyclopropanecarboxylic acid ester,
  (C) a step of contacting the mixture obtained in the step (B) with an aqueous alkali metal hydrogen sulfite solution to obtain an alkali metal salt of a trans-2,2-dimethyl-3-[(hydroxy)(sulfo)methyl]cyclopropanecarboxylic acid ester, and
  (D) a step of contacting the alkali metal salt obtained in the above-mentioned step (C) with a base or the like to obtain a trans-2,2-dimethyl-3-formylcyclopropanecarboxylic acid ester.

11 Claims, No Drawings

PROCESS FOR PRODUCTION OF TRANS-2, 2-DIMETHYL-3-FORMYLCYCLOPROPANE-CARBOXYLIC ACID ESTER

TECHNICAL FIELD

The present invention relates to a process for production of a trans-2,2-dimethyl-3-formylcyclopropanecarboxylic acid ester.

BACKGROUND ART

Trans-2,2-dimethyl-3-formylcyclopropanecarboxylic acid esters are useful compounds as intermediates of insecticides (e.g. J. Chem. Soc. (C), 1076 (1970)). As processes for production of the trans-2,2-dimethyl-3-formylcyclopropanecarboxylic acid ester, J. Chem. Soc. (C), 1076 (1970) discloses a process comprising oxidizing trans-chrysanthemic acid with ozone, and Tetrahedron, 57, 6083 (2001) discloses a process comprising treating a trans-2,2-dimethyl-3-(acyloxymethyl)cyclopropanecarboxylic acid ester with a base followed by conducting Swern oxidation.

DISCLOSURE OF THE INVENTION

The present invention provides

<1> A process for production of a trans-2,2-dimethyl-3-formylcyclopropanecarboxylic acid ester comprising:

(A) a step of reacting a trans-isomer of a 2,2-dimethyl-3-(acyloxymethyl)cyclopropanecarboxylic acid ester or a mixture of a trans- and cis-isomers thereof with at least one alkali metal compound selected from the group consisting of an alkali metal hydroxide, an alkali metal carbonate and an alkali metal alcoholate in the presence of an alcohol solvent to obtain a mixture containing a trans-2,2-dimethyl-3-(hydroxymethyl)cyclopropanecarboxylic acid ester, (B) a step of conducting an oxidation treatment of the mixture which contains a trans-2,2-dimethyl-3-(hydroxymethyl)cyclopropanecarboxylic acid ester and which is obtained in the above-mentioned step (A) to obtain a mixture containing a crude trans-2,2-dimethyl-3-formylcyclopropanecarboxylic acid ester, (C) a step of contacting the mixture obtained in the above-mentioned step (B) with an aqueous alkali metal hydrogen sulfite solution to obtain an alkali metal salt of a trans-2,2-dimethyl-3-[(hydroxy)(sulfo)methyl]cyclopropanecarboxylic acid ester, and (D) a step of contacting the alkali metal salt obtained in the above-mentioned step (C) with an acid, a base or a water-soluble aldehyde to obtain a trans-2,2-dimethyl-3-formylcyclopropanecarboxylic acid ester;

<2> The process according to <1>, wherein the step (B) is a step of contacting the mixture which contains a trans-2,2-dimethyl-3-(hydroxymethyl)cyclopropanecarboxylic acid ester and which is obtained in the above-mentioned step (A), a nitroxy radical compound and an oxidizing agent;

<3> The process according to <2>, wherein the oxidizing agent is at least one selected from the group consisting of a salt of hypohalous acid, N-halosuccinimide, trichloroisocyanuric acid and iodine;

<4> The process according to any one of <1> to <3>, wherein a mixture of a trans- and cis-isomers of a 2,2-dimethyl-3-(acyloxymethyl)cyclopropanecarboxylic acid ester is used in the step (A);

<5> The process according to any one of <1> to <5>, wherein the step (B) is conducted after concentrating the mixture which contains a trans-2,2-dimethyl-3-(hydroxymethyl) cyclopropanecarboxylic acid ester and which is obtained in the above-mentioned step (A);

<6> The process according to <5>, wherein the concentration is conducted after treating the mixture which contains a trans-2,2-dimethyl-3-(hydroxymethyl)cyclopropanecarboxylic acid ester and which is obtained in the above-mentioned step (A), with an acid;

<7> The process according to <4>, wherein the mixture of a trans- and cis-isomers of a 2,2-dimethyl-3-(acyloxymethyl)cyclopropanecarboxylic acid ester is one obtained by reacting a 1-(acyloxy)-3-methyl-2-butene with a diazoacetic acid ester in the presence of an metal catalyst;

<8> The process according to <7>, wherein the reaction of the 1-(acyloxy)-3-methyl-2-butene and the diazoacetic acid ester is conducted under the condition where the amount of water is 0.1% by weight or less per 1 part by weight of the diazoacetic acid ester;

<9> The process according to <7>, wherein the reaction of the 1-(acyloxy)-3-methyl-2-butene and the diazoacetic acid ester is conducted by contacting a composition comprising the 1-(acyloxy)-3-methyl-2-butene and the diazoacetic acid ester with a metal catalyst;

<10> The process according to <9>, wherein the amount of water in the composition comprising the 1-(acyloxy)-3-methyl-2-butene and the diazoacetic acid ester is 0.1% by weight or less per 1 part by weight of the diazoacetic acid ester;

<11> The process according to <9> or <10>, wherein the composition comprising the 1-(acyloxy)-3-methyl-2-butene and the diazoacetic acid ester is one obtained by reacting a hydrochloric acid salt of a glycine ester with sodium nitrite in the presence of a 1-(acyloxy)-3-methyl-2-butene and an acid catalyst followed by dehydrating the obtained organic layer;

<12> A composition comprising a 1-(acyloxy)-3-methyl-2-butane and a diazoacetic acid ester wherein the amount of water is 0.1% by weight or less per 1 part by weight of the diazoacetic acid ester, and the like.

BEST MODE FOR CARRYING OUT THE PRESENT INVENTION

First, the step (A) will be illustrated. The step (A) is a step of reacting a trans-isomer of a 2,2-dimethyl-3-(acyloxymethyl)cyclopropanecarboxylic acid ester or a mixture of a trans- and cis-isomers thereof with at least one alkali metal compound selected from the group consisting of an alkali metal hydroxide, an alkali metal carbonate and an alkali metal alcoholate in the presence of an alcohol solvent to obtain a mixture containing a trans-2,2-dimethyl-3-(hydroxymethyl) cyclopropanecarboxylic acid ester.

A trans-isomer of a 2,2-dimethyl-3-(acyloxymethyl)cyclopropanecarboxylic acid ester means one having a structure where the acyloxymethyl group at 3-position and the alkoxycarbonyl group at 1-position on the opposite side with respect to the cyclopropane ring plane and a cis-isomer thereof means one having a structure where the acyloxymethyl group at 3-position and the alkoxycarbonyl group at 1-position on the same side with respect to the cyclopropane ring plane.

In the step (A), a mixture of a trans- and cis-isomers of a 2,2-dimethyl-3-(acyloxymethyl)cyclopropanecarboxylic acid ester is preferably used. The ratio of the trans- and cis-isomers in the mixture of a trans- and cis-isomers of a 2,2-dimethyl-3-(acyloxymethyl)cyclopropanecarboxylic acid ester is not particularly limited, and a mixture obtained by mixing the trans- and cis-isomers in any ratio is used. A mixture containing larger amount of the trans-isomer than that of the cis-isomer is preferably used.

As the trans-isomer of a 2,2-dimethyl-3-(acyloxymethyl) cyclopropanecarboxylic acid ester, an optically active trans-isomer of a 2,2-dimethyl-3-(acyloxymethyl)cyclopropanecarboxylic acid ester may be used. Alternatively, a mixture of an optically active trans- and cis-isomers of a 2,2-dimethyl-3-(acyloxymethyl)cyclopropanecarboxylic acid ester may be used as the mixture of a trans- and cis-isomers of a 2,2-dimethyl-3-(acyloxymethyl)cyclopropanecarboxylic acid ester.

Examples of the acyl group of the acyloxymethyl group at 3-position include a C2-C10 aliphatic or aromatic acyl group such as an acetyl group, a propionyl group and a benzoyl group. Examples of the alkoxy group of the alkoxycarbonyl group at 1-position include a linear, branched chain or cyclic C1-C6 alkoxy group such as a methoxy group, an ethoxy group, an n-propoxy group, an isopropoxy group, a tert-butoxy group, an n-pentyloxy group, an n-hexyloxy group and a cyclohexyloxy group.

Examples of the 2,2-dimethyl-3-(acyloxymethyl)cyclopropanecarboxylic acid ester include methyl 2,2-dimethyl-3-(acetoxymethyl)cyclopropanecarboxylate, methyl 2,2-dimethyl-3-(benzoyloxymethyl)cyclopropanecarboxylate, ethyl 2,2-dimethyl-3-(acetoxymethyl)cyclopropanecarboxylate, ethyl 2,2-dimethyl-3-(benzoyloxymethyl)cyclopropanecarboxylate, n-propyl 2,2-dimethyl-3-(acetoxymethyl)cyclopropanecarboxylate, n-propyl 2,2-dimethyl-3-(benzoyloxymethyl)cyclopropanecarboxylate, isopropyl 2,2-dimethyl-3-(acetoxymethyl)cyclopropanecarboxylate, ispropyl 2,2-dimethyl-3-(benzoyloxymethyl)cyclopropanecarboxylate, n-butyl 2,2-dimethyl-3-(acetoxymethyl)cyclopropanecarboxylate, n-butyl 2,2-dimethyl-3-(benzoyloxymethyl)cyclopropanecarboxylate, isobutyl 2,2-dimethyl-3-(acetoxymethyl)cyclopropanecarboxylate, isobutyl 2,2-dimethyl-3-(benzoyloxymethyl)cyclopropanecarboxylate, tert-butyl 2,2-dimethyl-3-(acetoxymethyl)cyclopropanecarboxylate, tert-butyl 2,2-dimethyl-3-(benzoyloxymethyl)cyclopropanecarboxylate, n-pentyl 2,2-dimethyl-3-(acetoxymethyl)cyclopropanecarboxylate, n-pentyl 2,2-dimethyl-3-(benzoyloxymethyl)cyclopropanecarboxylate, n-hexyl 2,2-dimethyl-3-(acetoxymethyl)cyclopropanecarboxylate, n-hexyl 2,2-dimethyl-3-(benzoyloxymethyl)cyclopropanecarboxylate, cyclohexyl 2,2-dimethyl-3-(acetoxymethyl)cyclopropanecarboxylate and cyclohexyl 2,2-dimethyl-3-(benzoyloxymethyl)cyclopropanecarboxylate.

Examples of the alkali metal hydroxide include sodium hydroxide and potassium hydroxide. Examples of the alkali metal carbonate include sodium carbonate and potassium carbonate. Examples of the alkali metal alcoholate include a C1-C6 alkali metal alcoholate such as sodium methylate, sodium ethylate, potassium methylate and potassium ethylate. While at least one selected from the group consisting of the alkali metal hydroxide, the alkali metal carbonate and the alkali metal alcoholate is used as the alkali metal compound, at least one selected from the group consisting of the alkali metal carbonate and the alkali metal alcoholate is preferable and the alkali metal alcoholate is more preferable.

A commercially available alkali metal compound can be used.

The used amount of the alkali metal compound is usually 0.01 to 50 parts by weight per 1 part by weight of the trans-isomer of the 2,2-dimethyl-3-(acyloxymethyl)cyclopropanecarboxylic acid ester or a mixture of the trans- and cis-isomers thereof.

Examples of the alcohol solvent include a C1-C6 lower alcohol solvent such as methanol, ethanol, 1-propanol, 2-propanol and 1-butanol.

The used amount of the alcohol solvent is usually 1 to 100 parts by weight and preferably 2 to 50 parts by weight per 1 part by weight of the trans-isomer of the 2,2-dimethyl-3-(acyloxymethyl)cyclopropanecarboxylic acid ester or a mixture of the trans- and cis-isomers thereof.

The reaction temperature is usually in a range of $-20°$ C. to a boiling point of the alcohol solvent.

The reaction time is usually 0.5 to 10 hours.

Thus, a mixture containing a trans-2,2-dimethyl-3-(hydroxymethyl)cyclopropanecarboxylic acid ester is obtained. When a mixture of a trans- and cis-isomers of 2,2-dimethyl-3-(acyloxymethyl)cyclopropanecarboxylic acid ester is used, a mixture containing a cis-2,2-dimethyl-3-(hydroxymethyl)cyclopropanecarboxylic acid ester and 6,6-dimethyl-3-oxabicyclo[3.1.0]hexan-2-one in addition to the trans-2,2-dimethyl-3-(hydroxymethyl)cyclopropanecarboxylic acid ester is usually obtained.

Meanwhile, the 2,2-dimethyl-3-(acyloxymethyl)cyclopropanecarboxylic acid ester or the produced 2,2-dimethyl-3-(hydroxymethyl)cyclopropanecarboxylic acid ester is sometimes reacted with the used alcohol solvent to be progressed a transesterification reaction depending on the kinds of the alkali metal compound used, and a mixture containing a trans-2,2-dimethyl-3-(hydroxymethyl)cyclopropanecarboxylic acid ester having a different ester part from that of trans-2,2-dimethyl-3-(acyloxymethyl)cyclopropanecarboxylic acid ester, which is a raw material, is sometimes obtained. Especially, when the alkali metal hydroxide or the alkali metal alcoholate is used as the alkali metal compound, the transesterification reaction easily proceeds. For example, when an ethyl trans-2,2-dimethyl-3-(acyloxymethyl)cyclopropanecarboxylate is reacted with sodium methylate in methanol solvent, a mixture containing a methyl trans-2,2-dimethyl-3-(acyloxymethyl)cyclopropanecarboxylate is usually obtained.

The obtained mixture may be used as it is for the next step (B). If this is the case, the obtained mixture is preferably used for the next step (B) after removing the alcohol solvent from the mixture since an oxidation reaction of the alcohol solvent contained in the mixture also proceeds in the next step (B). The removal of the alcohol solvent may be conducted by concentrating the mixture, and by, if necessary adding a water-insoluble organic solvent, and washing with water. When the mixture was concentrated to remove the alcohol solvent, the mixture is preferably treated with an acid followed by removing the alcohol solvent by concentration from the viewpoint of the stability of the trans-2,2-dimethyl-3-(hydroxymethyl)cyclopropanecarboxylic acid ester on the concentration.

The acid treatment of the mixture is usually conducted by mixing the mixture with an acid.

Examples of the acid include a mineral acid such as hydrochloric acid and sulfuric acid. The used amount thereof is usually 0.8 to 5 moles and preferably 0.9 to 2 moles per 1 mole of the alkali metal compound used in the step (A).

The temperature of the acid treatment is usually $-20$ to $70°$ C.

Next, the step (B) will be illustrated. The step (B) is a step of conducting an oxidation treatment of the mixture which contains a trans-2,2-dimethyl-3-(hydroxymethyl)cyclopropanecarboxylic acid ester and which is obtained in the above-mentioned step (A) to obtain a mixture containing a crude trans-2,2-dimethyl-3-formylcyclopropanecarboxylic acid ester. While the oxidation treatment of the mixture which contains a trans-2,2-dimethyl-3-(hydroxymethyl)cyclopropanecarboxylic acid ester and which is obtained in the above-mentioned step (A) as it is may be conducted, the oxidation treatment of a mixture which contains a trans-2,2-dimethyl-3-(hydroxymethyl)cyclopropanecarboxylic acid ester and which is obtained by removing the alcohol solvent from the reaction mixture as described above, may be conducted, and the oxidation treatment of a mixture which contains a trans-2,2-dimethyl-3-(hydroxymethyl)cyclopropanecarboxylic acid ester and which is obtained by treating the reaction mixture with an acid followed by removing the alcohol solvent may be conducted. The mixture which contains a trans-2,2-dimethyl-3-(hydroxymethyl)cyclopropanecarboxylic acid ester and which is obtained by removing the alcohol solvent from the reaction mixture is preferably used, and the mixture which contains a trans-2,2-dimethyl-3-(hydroxymethyl)cyclopropanecarboxylic acid ester and which is obtained by treating the reaction mixture with an acid followed by removing the alcohol solvent is more preferably used.

Herein, "trans" means a structure where the alkoxycarbonyl group at 1-position and the formyl group at 3-position on the opposite side with respect to the cyclopropane ring plane and "cis" means a structure where the alkoxycarbonyl group at 1-position and the formyl group at 3-position on the same side with respect to the cyclopropane ring plane.

The oxidation treatment is not particularly limited in so far as it is a process comprising oxidizing a primary alcohol to convert into the corresponding aldehyde. Examples thereof include a process using a nitroxy radical compound and an oxidizing agent (e.g. JP 2004-99595 A), a process using dimethyl sulfoxide (e.g. Tetrahedron, 57, 6083 (2001)) and a process using pyridinium chromate (Heterocyces, 23, 2859 (1985)). From the industrial viewpoint, the process using a nitroxy radical and an oxidizing agent is preferable. The process using a nitroxy radical compound and an oxidizing agent will be illustrated below.

Examples of the nitroxy radical compound include 2,2,6,6-tetramethylpiperidin-1-oxyl, 4-acetoxy-2,2,6,6-tetramethylpiperidin-1-oxyl, 4-propionyloxy-2,2,6,6-tetramethylpiperidin-1-oxyl, 4-benzoyloxy-2,2,6,6-tetramethylpiperidin-1-oxyl, 4-methoxy-2,2,6,6-tetramethylpiperidin-1-oxyl, 4-ethoxy-2,2,6,6-tetramethylpiperidin-1-oxyl, 4-benzyloxy-2,2,6,6-tetramethylpiperidin-1-oxyl, 4-acetamide-2,2,6,6-tetramethylpiperidin-1-oxyl, 4-oxo-2,2,6,6-tetramethylpiperidin-1-oxyl and 2,2,5,5-tetramethylpyrrolidin-1-oxyl.

A commercially available nitroxy radical compound may be used and one produced according to known methods, for example, JP 2002-145861 A, may be used.

The nitroxy radical compound may be used as it is, and may be dissolved or suspended in the solvent described below to use.

The used amount of the nitroxy radical compound is usually 0.0001 to 0.1 mole and preferably 0.001 to 0.01 mole per 1 mole of sum of the trans- and cis-2,2-dimethyl-3-(hydroxymethyl)cyclopropanecarboxylic acid esters in the mixture which contains a trans-2,2-dimethyl-3-(hydroxymethyl) cyclopropanecarboxylic acid ester and which is obtained in the above-mentioned step (A).

Examples of the oxidizing agent include a salt of hypohalous acid, N-halosuccinimide, trichloroisocyanuric acid and iodine, and the salt of hypohalous acid is preferable. Examples of the salt of hypohalous acid include an alkali metal salt of hypohalous acid such as sodium hypochlorite and potassium hypochlorite, and an alkaline earth metal salt of hypohalous acid such as calcium hypochlorite and sodium hypobromite, and the alkali metal salt of hypohalous acid is preferable and an alkali metal hypochlorite is more preferable and sodium hypochlorite is especially preferable. Examples of N-halosuccinimide include N-chlorosuccinimide and N-bromosuccinimide.

The oxidizing agents may be used alone and two or more thereof may be mixed to use.

Each of the oxidizing agents may be used as it is, and a solution thereof such as an aqueous solution thereof may be used.

When the used amount of the oxidizing agent is too much, side reactions easily proceed, and therefore, it is usually 0.5 to 2.5 moles and preferably 0.7 to 1.8 moles per 1 mole of sum of the trans- and cis-2,2-dimethyl-3-(hydroxymethyl)cyclopropanecarboxylic acid esters in the mixture which contains a trans-2,2-dimethyl-3-(hydroxymethyl)cyclopropanecarboxylic acid ester and which is obtained in the above-mentioned step (A).

The oxidation treatment using the nitroxy radical compound and the oxidizing agent is usually conducted by mixing the mixture which contains a trans-2,2-dimethyl-3-(hydroxymethyl)cyclopropanecarboxylic acid ester and which is obtained in the above-mentioned step (A), the nitroxy radical compound and the oxidizing agent, and the mixing order is not particularly limited.

The oxidation treatment is preferably conducted with keeping pH of a reaction mixture obtained by mixing the mixture which contains a trans-2,2-dimethyl-3-(hydroxymethyl)cyclopropanecarboxylic acid ester and which is obtained in the above-mentioned step (A), the nitroxy radical compound and the oxidizing agent in a range of 6 to 13, more preferably in a range of 6 to 10 and much more preferably in a range of 8 to 10. The adjustment of pH is usually conducted using a mineral acid, an organic acid, a hydrogen carbonate and a phosphate.

Examples of the mineral acid include hydrochloric acid, sulfuric acid, phosphoric acid and boric acid. Examples of the organic acid include acetic acid, propionic acid, benzoic acid and p-toluenesulfonic acid. Examples of the hydrogen carbonate include an alkali metal hydrogen carbonate such as sodium hydrogen carbonate and potassium hydrogen carbonate. Examples of the phosphate include an alkali metal phosphate such as potassium dihydrogen phosphate, dipotassium hydrogen phosphate, sodium dihydrogen phosphate and disodium hydrogen phosphate. These may be used as it is and an aqueous solution thereof may be used.

The oxidation treatment may be conducted in the presence of an alkali metal halide such as potassium bromide and sodium bromide. The used amount thereof is usually 0.01 to 0.3 mole and preferably 0.05 to 0.25 mole per 1 mole of the oxidizing agent.

The oxidation treatment is usually carried out in the presence of a solvent. The solvent is not particularly limited in so far as it is an inert solvent on the reaction. Examples thereof include water; an aromatic hydrocarbon solvent such as toluene, xylene and mesitylene; a halogenated hydrocarbon solvent such as dichloromethane, chloroform, carbon tetrachloride and 1,2-dichloroethane; an ether solvent such as diethyl ether, diisopropyl ether and methyl tert-butyl ether; and a ketone solvent such as methyl isobutyl ketone and methyl tert-butyl ketone. The solvent may be used alone and two or more may be mixed to use. The used amount of the solvent is not particularly limited.

The treatment temperature is usually −5 to 50° C. The treatment time is usually 1 to 50 hours.

A reaction mixture containing a crude trans-2,2-dimethyl-3-formylcyclopropanecarboxylic acid ester is obtained by the oxidation treatment. When the mixture which contains the trans-2,2-dimethyl-3-(hydroxymethyl)cyclopropanecarboxylic acid ester and which is obtained in the above-mentioned step (A), also includes a cis-2,2-dimethyl-3-(hydroxymethyl)cyclopropanecarboxylic acid ester, the above-mentioned reaction mixture usually includes a cis-2,2-dimethyl-3-formylcyclopropanecarboxylic acid ester.

The reaction mixture may be used as it is for the next step (C). When the unreacted oxidizing agent remains in the mixture, the residual oxidizing agent reacts with an alkali metal hydrogen sulfite used in the next step (C), and therefore, a mixture which contains a crude trans-2,2-dimethyl-3-formylcyclopropanecarboxylic acid ester and which is obtained by contacting the mixture with an reducing agent such as sodium thiosulfate to decompose the residual oxidizing agent, is preferably used for the next step (C). Alternatively, a mixture which contains a crude trans-2,2-dimethyl-3-formylcyclopropanecarboxylic acid ester and which is obtained by decomposing the residual oxidizing agent followed by, if necessary adding water or a water-insoluble solvent thereto, and extracting is also preferably used for the next step (C).

Next, the step (C) will be illustrated. The step (C) is a step of contacting the mixture which contains a crude trans-2,2-dimethyl-3-formylcyclopropanecarboxylic acid ester and which is obtained in the above-mentioned step (B), with an aqueous alkali metal hydrogen sulfite solution to obtain an alkali metal salt of a trans-2,2-dimethyl-3-[(hydroxy)(sulfo)methyl]cyclopropanecarboxylic acid ester.

Examples of the alkali metal hydrogen sulfite include sodium hydrogen sulfite and potassium hydrogen sulfite. While the concentration of the alkali metal hydrogen sulfite in the aqueous alkali metal hydrogen sulfite solution is not particularly limited, it is usually 5 to 35% by weight.

The used amount of the alkali metal hydrogen sulfite is usually 0.8 mole or more per 1 mole of sum of a trans- and cis-2,2-dimethyl-3-formylcyclopropanecarboxylic acid esters in the mixture containing a crude trans-2,2-dimethyl-3-formylcyclopropanecarboxylic acid ester, and there is no specific upper limit. From the economic viewpoint, the practical used amount thereof is 1 to 2 moles per 1 mole of sum of a trans- and cis-2,2-dimethyl-3-formylcyclopropanecarboxylic acid esters in the above-mentioned mixture.

While the mixture containing a crude trans-2,2-dimethyl-3-formylcyclopropanecarboxylic acid ester may be contacted with an aqueous alkali metal hydrogen sulfite solution in the absence of an organic solvent, the contact is preferably conducted in the presence of a water-nonmiscible organic solvent. Examples of the water-nonmiscible organic solvent include an aromatic hydrocarbon solvent such as toluene, xylene and mesitylene; an aliphatic hydrocarbon solvent such as pentane, hexane, heptane, octane and cyclohexane; an ester solvent such as ethyl acetate and methyl benzoate; a halogenated hydrocarbon solvent such as dichloromethane, dichloroethane, carbon tetrachloride and chlorobenzene; a nitrile solvent such as benzonitrile; and an ether solvent such as diethyl ether. The water-nonmiscible organic solvent may be used alone and two or more thereof may be mixed to use. While the used amount of the water-nonmiscible organic solvent is not particularly limited, it is usually 0.5 to 10 parts by weight and preferably 1 to 5 parts by weight per 1 part by weight of sum of trans- and cis-2,2-dimethyl-3-formylcyclopropanecarboxylic acid esters.

The contacting temperature is usually 0 to 80° C. and preferably 10 to 50° C. The contacting time is usually 1 to 5 hours.

The contact of the mixture containing a crude trans-2,2-dimethyl-3-formylcyclopropanecarboxylic acid ester with the alkali metal hydrogen sulfite is usually conducted at normal pressure and may be conducted under pressure. The progress of the reaction can be checked by a conventional analytical means such as gas chromatography, high performance liquid chromatography and thin layer chromatography.

After completion of the reaction, an aqueous layer containing an alkali metal salt of a trans-2,2-dimethyl-3-[(hydroxy)(sulfo)methyl]cyclopropanecarboxylic acid ester can be obtained by, if necessary adding a water-nonmiscible organic solvent to the reaction mixture, and separating. The obtained aqueous layer containing the alkali metal salt may be used as it is for the next step (D) and may be used for the next step (D) after washing with a water-nonmiscible organic solvent. Alternatively, the aqueous layer may be concentrated until the alkali metal salt is not precipitated to use for the next step (D). Alternatively, the alkali metal salt of a trans-2,2-dimethyl-3-[(hydroxy)(sulfo)methyl]cyclopropanecarboxylic acid ester is isolated by concentrating the aqueous layer containing the alkali metal salt to use for the next step (D).

Examples of the obtained alkali metal salt of the trans-2,2-dimethyl-3-[(hydroxy)(sulfo)methyl]cyclopropanecarboxylic acid ester include sodium salt of methyl trans-2,2-dimethyl-3-[(hydroxy)(sulfo)methyl]cyclopropanecarboxylate, sodium salt of methyl trans-2,2-dimethyl-3-[(hydroxy)(sulfo)methyl]cyclopropanecarboxylate, sodium salt of ethyl trans-2,2-dimethyl-3-[(hydroxy)(sulfo)methyl]cyclopropanecarboxylate, sodium salt of n-propyl trans-2,2-dimethyl-3-[(hydroxy)(sulfo)methyl]cyclopropanecarboxylate, sodium salt of isopropyl trans-2,2-dimethyl-3-[(hydroxy)(sulfo)methyl]cyclopropanecarboxylate, sodium salt of n-butyl trans-2,2-dimethyl-3-[(hydroxy)(sulfo)methyl]cyclopropanecarboxylate, sodium salt of isobutyl trans-2,2-dimethyl-3-[(hydroxy)(sulfo)methyl]cyclopropanecarboxylate, sodium salt of tert-butyl trans-2,2-dimethyl-3-[(hydroxy)(sulfo)methyl]cyclopropanecarboxylate, sodium salt of n-pentyl trans-2,2-dimethyl-3-[(hydroxy)(sulfo)methyl]cyclopropanecarboxylate, sodium salt of n-hexyl trans-2,2-dimethyl-3-[(hydroxy)(sulfo)methyl]cyclopropanecarboxylate, sodium salt of cyclohexyl trans-2,2-dimethyl-3-[(hydroxy)(sulfo)methyl]cyclopropanecarboxylate, and the above-mentioned each salt of which sodium is changed to potassium (for example, potassium salt of methyl trans-2,2-dimethyl-3-[(hydroxy)(sulfo)methyl]cyclopropanecarboxylate, etc.) and the like.

Next, the step (D) will be illustrated. The step (D) is a step of contacting the alkali metal salt obtained in the above-mentioned step (C) with an acid, a base or a water-soluble aldehyde to obtain a trans-2,2-dimethyl-3-formylcyclopropanecarboxylic acid ester.

Examples of the acid include an inorganic acid such as hydrochloric acid, sulfuric acid and nitric acid, and a sulfonic acid such as methanesulfonic acid.

Examples of the base include an alkali metal hydroxide such as sodium hydroxide and potassium hydroxide, an alkali metal carbonate such as sodium carbonate and potassium carbonate, and an alkali metal hydrogen carbonate such as sodium hydrogen carbonate and potassium hydrogen carbonate, and the alkali metal hydroxide and the alkali metal carbonate are preferable.

Examples of the water-soluble aldehyde include a monomer of the water-soluble aldehyde such as formaldehyde and acetaldehyde, and a polymer of the water-soluble aldehyde such as trioxane, paraformaldehyde and paraldehyde.

Each of these acids, bases and water-soluble aldehydes may be used as it is and in a form of an aqueous solution. The aqueous solution thereof is preferably used.

Among them, the base and the water-soluble aldehyde are preferable.

The contact of the alkali metal salt with the acid, the base or the water-soluble aldehyde is usually conducted in the presence of a water-nonmiscible organic solvent and water.

While the used amount of water is not particularly limited, it is usually 0.5 to 20 parts by weight and preferably 1 to 5 parts by weight per 1 part of the alkali metal salt. When an aqueous layer containing the alkali metal salt is used, the used amount of water may be accordingly decided in consideration to the amount of water in the aqueous layer. Alternatively, when the aqueous solution of the acid, the base or the water-soluble aldehyde is used, the used amount of water may be accordingly decided in consideration to the amount of water in these aqueous solutions.

Examples of the water-nonmiscible organic solvent include the same as described above. While the used amount thereof is not particularly limited, it is usually 0.5 to 10 parts by weight and preferably 1 to 5 parts by weight per 1 part of the alkali metal salt.

When the acid is used, the used amount of the acid is usually 0.8 to 1.5 molar equivalent per 1 mole of the alkali metal salt.

When the base is used, the used amount of the base is usually 0.8 molar equivalent or more per 1 mole of the alkali metal salt. When the used amount of the base is too much, the trans-2,2-dimethyl-3-formylcyclopropanecarboxylic acid ester produced is easily decomposed, and therefore, practically, the base is preferable used in an amount by which pH of an aqueous layer of the reaction mixture is adjusted in a range of 9 to 11, and more preferably in a range of 9.5 to 10.5.

Meanwhile, in the present description, the molar equivalent means a value obtained by multiplying a number of moles of the acid or base by the valence. For example, when 0.5 mole of sulfuric acid is used per 1 mole of the alkali metal salt, the used amount of sulfuric acid is 1 molar equivalent, and when 0.5 mole of potassium carbonate is used per 1 mole of the alkali metal salt, the used amount of potassium carbonate is 1 molar equivalent When the water-soluble aldehyde is used, the used amount thereof is usually 0.8 mole or more per 1 mole of the alkali metal salt. While the used amount thereof is not particularly limited, it is practically 1 to 3 moles per 1 mole of the alkali metal salt from an economic viewpoint. When the polymer such as paraformaldehyde is used, the polymer is converted to the corresponding monomer based on the polymerization degree and the polymer in an amount of 0.8 mole or more as the monomer per 1 mole of the alkali metal salt is usually used. For example, when trioxane is used, 1 mole of trioxane is converted to 3 moles of formaldehyde, and the used amount may be decided. Alternatively, when the polymerization degree of the polymer is not clear, the used amount thereof may be decided assuming that a value obtained by dividing the weight of the polymer by the molecular weight of the corresponding monomer is number of moles of the corresponding monomer.

The contacting temperature of the alkali metal salt with the acid, the base or the water-soluble aldehyde is usually 0 to 80° C., and preferably 20 to 60° C. The contacting time is usually 1 to 5 hours.

The contact of the alkali metal salt with the acid, the base or the water-soluble aldehyde is usually conducted by mixing the alkali metal salt with the acid, the base or the water-soluble aldehyde in the presence of the water-nonmiscible organic solvent and water. While the mixing order is not particularly limited, the acid, the base or the water-soluble aldehyde is preferably added to a mixture of the water-nonmiscible organic solvent, water and the alkali metal salt. Alternatively, the reaction is usually conducted at normal pressure and may be conducted under pressure. The progress of the reaction can be checked by a conventional analytical means such as gas chromatography, high performance liquid chromatography and thin layer chromatography.

After completion of the reaction, for example, an organic layer containing the trans-2,2-dimethyl-3-formylcyclopropanecarboxylic acid ester can be obtained by separating the reaction mixture, and the trans-2,2-dimethyl-3-formylcyclopropanecarboxylic acid ester can be isolated by, for example, concentrating the obtained organic layer.

Alternatively, the trans-2,2-dimethyl-3-formylcyclopropanecarboxylic acid ester obtained may be further purified by a conventional purification means such as distillation, recrystallization and column chromatography.

Alternatively, when the 2,2-dimethyl-3-(acyloxymethyl)cyclopropanecarboxylic acid ester used in the above-mentioned step (A) is an optically active isomer, the trans-2,2-dimethyl-3-formylcyclopropanecarboxylic acid ester obtained is usually also an optically active isomer, and the configuration thereof is maintained.

Examples of the trans-2,2-dimethyl-3-formylcyclopropanecarboxylic acid ester include methyl trans-2,2-dimethyl-3-formylcyclopropanecarboxylate, ethyl trans-2,2-dimethyl-3-formylcyclopropanecarboxylate, n-propyl trans-2,2-dimethyl-3-formylcyclopropanecarboxylate, isopropyl trans-2,2-dimethyl-3-formylcyclopropanecarboxylate, n-butyl trans-2,2-dimethyl-3-formylcyclopropanecarboxylate, isobutyl trans-2,2-dimethyl-3-formylcyclopropanecarboxylate, sec-butyl trans-2,2-dimethyl-3-formylcyclopropanecarboxylate, tert-butyl trans-2,2-dimethyl-3-formylcyclopropanecarboxylate, n-pentyl trans-2,2-dimethyl-3-formylcyclopropanecarboxylate, n-hexyl trans-2,2-dimethyl-3-formylcyclopropanecarboxylate and cyclohexyl trans-2,2-dimethyl-3-formylcyclopropanecarboxylate.

Finally, a process for producing the mixture of a trans- and cis-isomers of a 2,2-dimethyl-3-(acyloxymethyl)cyclopropanecarboxylic acid ester used in the step (A) will be illustrated.

While the mixture of a trans- and cis-isomers of a 2,2-dimethyl-3-(acyloxymethyl)cyclopropanecarboxylic acid ester produced by any known methods can be used, a mixture of a trans- and cis-isomers of a 2,2-dimethyl-3-(acyloxymethyl)cyclopropanecarboxylic acid ester obtained by reacting a 1-(acyloxy)-3-methyl-2-butene with a diazoacetic acid ester in the presence of a metal catalyst is preferably used. The reaction will be illustrated below.

Examples of the metal catalyst include a monovalent or divalent copper compound such as copper(I) trifluoromethanesulfonate, copper(I) acetate, copper(I) bromide, copper(I) chloride, copper(I) iodide, copper(I) hydroxide, copper(II) trifluoromethanesulfonate, copper(II) acetate, copper(II) bromide, copper(II) chloride, copper(II) iodide and copper(II) hydroxide; a rhodium compound such as rhodium(II) acetate, rhodium(II) trifluoroacetate and rhodium(II) triphenylacetate; and a cobalt compound such as cobalt(II) chloride, cobalt(II) bromide and cobalt(II) acetate. Among them, the monovalent or divalent copper compound is preferable.

A copper complex obtained by reacting the above-mentioned monovalent or divalent copper compound with an optically active bisoxazoline compound (hereinafter, simply referred to as the bisoxazoline copper complex) can be also used as the metal catalyst. A mixture of trans- and cis-isomers of an optically active 2,2-dimethyl-3-(acyloxymethyl)cyclopropanecarboxylic acid ester is usually obtained by using the bisoxazoline copper complex. When an optically active 2,2-dimethyl-3-formylcyclopropanecarboxylic acid ester is desired, a mixture of trans- and cis-isomers of an optically active 2,2-dimethyl-3-(acyloxymethyl)cyclopropanecarboxylic acid ester produced using the bisoxazoline copper complex as the metal catalyst is preferably used in the step (A).

Examples of the optically active bisoxazoline compound include bis[2-[(4S)-tert-butyloxazoline]]methane, 2,2-bis[2-[(4S)-tert-butyloxazoline]]propane, 1,1-bis[2-[(4S)-tert-butyloxazoline]]cyclopropane and 1,1-bis[2-[(4S)-tert-butyloxazoline]]cyclohexane. Other examples thereof include these compounds of which the configuration (4S) at the 4-positon of the oxazoline ring is changed to (4R) such as bis[2-[(4R)-tert-butyloxazolinel]]methane.

The bisoxazoline copper complex is usually prepared by mixing the optically active bisoxazoline compound with the monovalent or divalent copper compound in the presence of a solvent.

The used amount of the optically active bisoxazoline compound is usually 0.8 to 5 moles and preferably 0.9 to 2 moles per 1 mole of the monovalent or divalent copper compound.

The bisoxazoline copper complex may be prepared in the presence of a fluorine-containing compound, and a mixture of a trans- and cis-isomers of a 2,2-dimethyl-3-(acyloxymethyl) cyclopropanecarboxylic acid ester having higher optical purity can be produced by using a bisoxazoline copper complex prepared in the presence of the fluorine-containing compound.

Examples of the fluorine-containing compound include hexafluorophosphates such as lithium hexafluorophosphate, sodium hexafluorophosphate, potassium hexafluorophosphate, silver hexafluorophosphate and trityl hexafluorophosphate; hexafluoroantimonates such as sodium hexafluoroantimonate, potassium hexafluoroantimonate, silver hexafluoroantimonate and trityl hexafluoroantimonate; (pentafluorophenyl)borates such as lithium tetrakis(pentafluorophenyl)borate, sodium tetrakis(pentafluorophenyl)borate, potassium tetrakis(pentafluorophenyl)borate, silver tetrakis(pentafluorophenyl)borate and trityl tetrakis(pentafluorophenyl)borate. The used amount of the fluorine-containing compound is usually 0.8 to 5 moles per 1 mole of the copper compound.

The preparation of the bisoxazoline copper complex is usually conducted in the presence of a solvent. Examples of the solvent include a halogenated hydrocarbon solvent such as dichloromethane, dichloroethane, chloroform and carbon tetrachloride; an aromatic hydrocarbon solvent such as benzene, toluene and xylene; and an ester solvent such as methyl acetate and ethyl acetate. When the 1-(acyloxy)-3-methyl-2-butene is a liquid, the 1-(acyloxy)-3-methyl-2-butane may be used as the solvent. The used amount of the solvent is usually 10 to 500 parts by weight per 1 part by weight of the copper compound.

The preparation of the bisoxazoline copper complex is usually carried out by mixing the solvent, the optically active bisoxazoline compound, the monovalent or divalent copper compound and if necessary the fluorine-containing compound, under an atmosphere of an inert gas such as argon and nitrogen. The preparation temperature is usually –20 to 100° C.

The obtained reaction solution containing the bisoxazoline copper complex may be used as it is for the reaction of the 1-(acyloxy)-3-methyl-2-butene and the diazoacetic acid ester, and the bisoxazoline copper complex isolated by concentrating the reaction solution may be used. Alternatively, the isolated bisoxazoline copper complex may be purified by a conventional purification means such as recrystallization to use.

Examples of the 1-(acyloxy)-3-methyl-2-butene include 3-methyl-2-butenyl acetate and 3-methyl-2-butenyl benzoate. The 1-(acyloxy)-3-methyl-2-butene can be produced according to known methods described in, for example, J. Org. Chem., 55, 5312 (1990) and the like.

Examples of the diazoacetic acid ester include methyl diazoacetate, ethyl diazoacetate, n-propyl diazoacetate, isopropyl diazoacetate, n-butyl diazoacetate, isobutyl diazoacetate, tert-butyl diazoacetate, n-pentyl diazoacetate, n-hexyl diazoacetate and cyclohexyl diazoacetate. A commercially available diazoacetic acid ester may be used and one produced according to known methods described in, for example, Organic Synthesis Collective Volume 3, P. 392 and the like may be used. A solution containing the diazoacetic acid ester, which is obtained by reacting the corresponding hydrochloric acid salt of the glycine ester with sodium nitrite in the presence of a solvent and an acid catalyst, is preferably used, and one obtained by dehydrating the obtained solution containing the diazoacetic acid ester is more preferably used.

Examples of the solvent include an ether solvent such as diethyl ether and methyl tert-butyl ether; a halogenated hydrocarbon solvent such as dichloromethane, 1,2-dichloroethane and chloroform; an aliphatic hydrocarbon solvent such as hexane, heptane and octane; and an aromatic hydrocarbon solvent such as benzene and toluene. When the 1-(acyloxy)-3-methyl-2-butene is a liquid, the 1-(acyloxy)-3-methyl-2-butene may be used as the solvent. When the 1-(acyloxy)-3-methyl-2-butene is a liquid, the 1-(acyloxy)-3-methyl-2-butene is preferably used as the solvent.

While the method of dehydrating the obtained solution containing the diazoacetic acid ester is not particularly limited, an azeotropic dehydration method is preferable.

When the obtained solution containing the diazoacetic acid ester is dehydrated by the azeotropic dehydration method, the treating temperature is usually –20 to 100° C. and the treating pressure is usually 0.1 to 30 kPa. The conditions may be decided so that the amount of water in the solution containing the diazoacetic acid ester after dehydration will usually become 0.1% by weight or less and preferably 0.05% by weight or less per 1 part by weight of the diazoacetic acid ester. The amount of water can be measured by an ordinary water measurement means such as a method using a Karl Fischer water measuring apparatus.

The reaction of the 1-(acyloxy)-3-methyl-2-butene and the diazoacetic acid ester usually carried out by mixing the 1-(acyloxy)-3-methyl-2-butene, the diazoacetic acid ester and the metal catalyst under an atmosphere of an inert gas such as argon and nitrogen. While the mixing order is not particularly limited, the diazoacetic acid ester is usually added to a mixture of the metal catalyst and the 1-(acyloxy)-3-methyl-2-butene.

The used amount of the metal catalyst is usually 0.00001 to 0.5 mole and preferably 0.0001 to 0.05 mole per 1 mole of the diazoacetic acid ester in terms of a metal.

The used amount of the 1-(acyloxy)-3-methyl-2-butene is usually 1 mole or more and preferably 1.2 mole or more per 1 mole of the diazoacetic acid ester. There is no specific upper limit, and when the 1-(acyloxy)-3-methyl-2-butene is a liquid, large excess amount thereof may be used also to serve as the solvent.

The reaction temperature is usually 0 to 120° C. and preferably 5 to 100° C.

While a reaction mixture containing a 2,2-dimethyl-3-(acyloxymethyl)cyclopropanecarboxylic acid ester is thus obtained, the reaction mixture usually contains a mixture of a trans- and cis-isomers of the 2,2-dimethyl-3-(acyloxymethyl) cyclopropanecarboxylic acid ester. While it may be used as it is for the step (A), the mixture of a trans- and cis-isomers of the 2,2-dimethyl-3-(acyloxymethyl)cyclopropanecarboxylic acid ester isolated from the reaction mixture by an ordinary method such as distillation is preferably used for the step (A). One obtained by further purifying the isolated mixture of a trans- and cis-isomers of the 2,2-dimethyl-3-(acyloxymethyl) cyclopropanecarboxylic acid ester by an ordinary purification means such as rectification and column chromatography may be used for the step (A).

The trans-isomer of the 2,2-dimethyl-3-(acyloxymethyl) cyclopropanecarboxylic acid ester can be obtained by separating the trans- or cis-isomer of the 2,2-dimethyl-3-(acyloxymethyl)cyclopropanecarboxylic acid ester from the mixture thereof by known methods such as column chromatography.

EXAMPLES

The present invention is illustrated by Examples in more detail below, but the present invention is not limited to these Examples. The trans-isomer/cis-isomer ratio of the cyclopropane compound was calculated by gas chromatography area-percentage method. The optical purity was calculated based on the area ratio of liquid chromatography.

Reference Example 1

Into a reaction container purged with nitrogen, 340 parts by weight of glycine ethyl ester hydrochloric acid salt and 566 parts by weight of water were added. To the obtained aqueous solution, 343 parts by weight of 3-methyl-2-butenyl acetate was added and then, the resultant mixture was cooled at an inner temperature of 8° C. To the mixture, 6.4 parts by weight of 23% by weight sodium hydroxide solution was added to adjust pH to 4.7. To the obtained mixture, 574 parts by weight of 35% by weight aqueous sodium nitrite solution and 37 parts by weight of 24% by weight aqueous citric acid solution were added dropwise over 10 hours in parallel with keeping an inner temperature of 8 to 12° C. and pH of 4.5 to 4.8. The obtained reaction mixture was stirred for two hours at the same temperature and then, 217 parts by weight of 7% by weight aqueous sodium carbonate solution was added dropwise thereto to adjust pH of the reaction mixture to 9.2. To the reaction mixture, 141 parts by weight of toluene was added and the resultant mixture was stirred. After leaving at rest, an aqueous layer was separated to obtain 735 parts by weight of an organic layer containing ethyl diazoacetate. The organic layer was analyzed by gas chromatography internal standard method to find out the content of ethyl diazoacetate was 35.6% by weight.

The obtained organic layer containing ethyl diazoacetate was added into a separable flask, and an internal pressure was adjusted to 2 kPa, and then, 84 parts by weight of the fraction containing toluene as a main component was removed by heating. The pressure was returned to a normal pressure by nitrogen and 639 parts by weight of the 3-methyl-2-butenyl acetate solution containing ethyl diazoacetate was obtained.

The solution was analyzed by gas chromatography internal standard method to find out the content of ethyl diazoacetate was 35.2% by weight. The content of water in the solution was measured using a Karl Fischer coulometric titration water measuring apparatus to find out it was 0.0064% by weight.

Reference Example 2

To a reaction container purged with nitrogen, 0.0957 parts by weight of copper(I) chloride, 0.269 parts by weight of 1,1-bis[2-[(4S)-(tert-butyl)oxazoline]]cyclopropane and 0.847 parts by weight of trityl tetrakis(pentafluorophenyl) borate were added and 542 parts by weight of 3-methyl-2-butenyl acetate was further added to the resultant mixture. The obtained mixture was stirred at 20° C. for 30 minutes and then, the inner temperature thereof was adjusted to 28° C. To the mixture, 1.1 parts by weight of the 3-methyl-2-butenyl acetate solution containing 35% by weight ethyl diazoacetate, which was obtained in Reference Example 1, was added and generation of nitrogen gas was confirmed. Further, 495 parts by weight of the 3-methyl-2-butenyl acetate solution containing 35% by weight ethyl diazoacetate, which was obtained in Reference Example 1, was added dropwise over 6 hours at an inner temperature of 22° C. to the mixture. The obtained mixture was stirred at the same temperature for 30 minutes to obtain 997 parts by weight of a reaction mixture containing trans- and cis-isomers of ethyl 2,2-dimethyl-3-(acetoxymethyl)cyclopropanecarboxylate. The reaction mixture was analyzed by gas chromatography internal standard method to find out the content (sum of the trans- and cis-isomers) of ethyl 2,2-dimethyl-3-(acetoxymethyl)cyclopropanecarboxylate was 25.6% by weight.

Yield: 78% (based on ethyl diazoacetate).

Trans-isomer/cis-isomer ratio: 87/13

Optical purity: trans-isomer 96% e.e. ((+)-isomer), cis-isomer 33% e.e. ((+)-isomer)

The reaction mixture was washed three times with 128 parts by weight of 5% by weight aqueous sodium hydrogen carbonate solution and then, distilled at 1 kPa to obtain 264 parts by weight of an oily matter (distilled temperature: 117 to 120° C.). The fraction was analyzed by gas chromatography internal standard method to find out the content (sum of the trans- and cis-isomers) of ethyl 2,2-dimethyl-3-(acetoxymethyl)cyclopropanecarboxylate was 91.0% by weight.

Trans-isomer/cis-isomer ratio: 87/13

Optical purity: trans-isomer 96% e.e. ((+)-isomer), cis-isomer 33% e.e. ((+)-isomer)

Example 1

To a reaction container purged with nitrogen, 51.6 parts by weight of the oily matter containing trans- and cis-isomers of ethyl 2,2-dimethyl-3-(acetoxymethyl)cyclopropanecarboxylate (content: 89.2% by weight, trans-isomer/cis-isomer ratio: 87/13), which was obtained according to the same manner as Reference Example 2, and 315 parts by weight of methanol were added, and the obtained mixture was adjusted to 65° C. To the mixture, 9.7 parts by weight of 24% by weight sodium methylate methanol solution was added and then, the resultant mixture was stirred at the same temperature for 3 hours.

The obtained reaction mixture was cooled to 20° C. After adding 4.5 parts by weight of 35% by weight hydrochloric acid thereto, the mixture was heated at 66 to 80° C. to distil 324 parts by weight of a fraction which main component was methanol away. To the obtained residue, 63 parts by weight of toluene and 22 parts by weight of water were added and the resultant mixture was refluxed at 85 to 110° C. During this period, a refluxed liquid was contacted with water to separate to a toluene layer and an aqueous layer and the only toluene layer was returned back into the reaction container. The obtained mixture was analyzed by gas chromatography internal standard method to find out the content of methanol was 0.03% by weight.

The obtained mixture was cooled at 20° C. and then, 12.3 parts by weight of water was added thereto. The mixture was separated and the obtained organic layer was refluxed at 20 kPa at an inner temperature of 66 to 68° C. During this period, a refluxed liquid was separated to an aqueous layer and a toluene layer and the aqueous layer was removed and the only toluene layer was returned back into the reaction container. After checking no separation of the refluxed liquid to an aqueous layer and a toluene layer, the pressure was returned to a normal pressure and 93.7 parts by weight of a toluene solution containing methyl trans-2,2-dimethyl-3-(hydroxymethyl)cyclopropanecarboxylate was obtained. The toluene solution was analyzed by gas chromatography internal standard method to find out the content of methyl trans-2,2-dimethyl-3-(hydroxymethyl)cyclopropanecarboxylate was 30.7% by weight, the yield thereof was 97.8% (based on ethyl trans-2,2-dimethyl-3-(acetoxymethyl)cyclopropanecarboxylate). The content of 6,6-dimethyl-3-oxabicyclo [3.1.0]hexan-2-one was 3.6% by weight and the content of methyl cis-2,2-dimethyl-3-(hydroxymethyl)cyclopropanecarboxylate was 0.4% by weight.

Example 2

To a reaction container purged with nitrogen, 86.7 parts by weight of the toluene solution containing methyl trans-2,2-dimethyl-3-(hydroxymethyl)cyclopropanecarboxylate, which was obtained in Example 1, 0.0534 parts by weight of a 50% by weight toluene solution of 2,2,6,6-tetramethylpiperidin-1-oxyl and 17.8 parts by weight of 5% by weight of aqueous sodium hydrogen carbonate solution were added. The obtained mixture was cooled at an inner temperature of 0° C. with stirring. To the mixture, 134.7 parts by weight of 12% by weight aqueous sodium hypochlorite solution was dropwise over 20 hours in a pH range of 9 to 10 with aerating a nitrogen gas to a gas phase part. After completion of adding dropwise, the obtained mixture was stirred at the same temperature for 3.5 hours. To the obtained reaction mixture, 4.8 parts by weight of 20% by weight aqueous sodium thiosulfate solution was added to stir for 1 hour. After leaving at rest, the mixture was separated to obtain 89.3 parts by weight of a toluene solution containing methyl trans-2,2-dimethyl-3-formylcyclopropanecarboxylate. The toluene solution was analyzed by gas chromatography internal standard method to find out the content of methyl trans-2,2-dimethyl-3-formylcyclopropanecarboxylate was 28.1% by weight, the yield thereof was 93.7%. Alternatively, the content of 6,6-dimethyl-3-oxabicyclo[3.1.0]hexan-2-one was 3.5% by weight and the content of methyl cis-2,2-dimethyl-3-(hydroxymethyl)cyclopropanecarboxylate was 0.2% by weight.

Example 3

In a reaction container purged with nitrogen, 161.6 parts by weight of the toluene solution containing 45.0 parts by weight of methyl trans-2,2-dimethyl-3-formylcyclopropanecarboxylate (which contained 6,6-dimethyl-3-oxabicyclo[3.1.0] hexan-2-one in 3.5% by weight), and 50.3 parts by weight of water were mixed. To the obtained mixture, 102.8 parts by weight of 35% by weight aqueous sodium hydrogen sulfite solution was added dropwise over 6 hours at an inner temperature of 25° C. to stir for 1 hour at the same temperature. After leaving the reaction mixture at rest, the reaction mixture was separated to an organic layer and an aqueous layer. To the obtained aqueous layer, 67.5 parts by weight of toluene was added and the resultant mixture was heated to 50° C. and then 56.2 parts by weight of 23% by weight aqueous sodium hydroxide solution was added dropwise thereto over 2 hours to stir for 0.5 hour at the same temperature. The pH of the aqueous layer after completion of adding dropwise was 9.8. After leaving the obtained mixture at rest, the mixture was separated to an organic layer and an aqueous layer. To the obtained aqueous layer, 22.5 parts by weight of toluene and 2.0 parts by weight of 23% by weight aqueous sodium hydroxide solution were added and the resultant mixture was stirred at pH 10.0 at 50° C. for 0.5 hour. After leaving the obtained mixture at rest, the mixture was separated to an organic layer and an aqueous layer. Two organic layers obtained were mixed and 11.3 parts by weight of water and 0.045 part by weight of 2,6-di-tert-butyl-p-cresol were added to stir. After leaving the mixture at rest, an aqueous layer was separated to obtain 136.7 parts by weight of a toluene layer containing methyl trans-2,2-dimethyl-3-formylcyclopropanecarboxylate. The toluene layer was analyzed by gas chromatography internal standard method to find out the content of methyl trans-2,2-dimethyl-3-formylcyclopropanecarboxylate was 31.8% by weight. The content of 6,6-dimethyl-3-oxabicyclo[3.1.0]hexan-2-one was 0.65% by weight and the removal efficiency thereof was 85%.

INDUSTRIAL APPLICABILITY

According to the present invention, a trans-2,2-dimethyl-3-formylcyclopropanecarboxylic acid ester, which is useful as intermediates of insecticides, can be produced industrially advantageously.

The invention claimed is:

1. A process for production of a trans-2,2-dimethyl-3-formylcyclopropanecarboxylic acid ester comprising:
   (A) a step of reacting a trans-isomer of a 2,2-dimethyl-3-(acyloxymethyl)cyclopropanecarboxylic acid ester or a mixture of a trans- and cis-isomers thereof with at least one alkali metal compound selected from the group consisting of an alkali metal hydroxide, an alkali metal carbonate and an alkali metal alcoholate in the presence of an alcohol solvent to obtain a mixture containing a trans-2,2-dimethyl-3-(hydroxymethyl)cyclopropanecarboxylic acid ester,
   (B) a step of conducting an oxidation treatment of the mixture which contains a trans-2,2-dimethyl-3-(hydroxymethyl)cyclopropanecarboxylic acid ester and which is obtained in the above-mentioned step (A) to obtain a mixture containing a crude trans-2,2-dimethyl-3-formylcyclopropanecarboxylic acid ester,
   (C) a step of contacting the mixture obtained in the above-mentioned step (B) with an aqueous alkali metal hydrogen sulfite solution to obtain an alkali metal salt of a trans-2,2-dimethyl-3-[(hydroxy)(sulfo)methyl]cyclopropanecarboxylic acid ester, and
   (D) a step of contacting the alkali metal salt obtained in the above-mentioned step (C) with an acid, a base or a water-soluble aldehyde to obtain a trans-2,2-dimethyl-3-formylcyclopropanecarboxylic acid ester.

2. The process according to claim 1, wherein the step (B) is a step of contacting the mixture which contains a trans-2,2-dimethyl-3-(hydroxymethyl)cyclopropanecarboxylic acid ester and which is obtained in the above-mentioned step (A), a nitroxy radical compound and an oxidizing agent.

3. The process according to claim 2, wherein the oxidizing agent is at least one selected from the group consisting of a salt of hypohalous acid, N-halosuccinimide, trichloroisocyanuric acid and iodine.

4. The process according to claim 1, wherein a mixture of a trans- and cis-isomers of a 2,2-dimethyl-3-(acyloxymethyl) cyclopropanecarboxylic acid ester is used in the step (A).

5. The process according to claim 1, wherein the step (B) is conducted after concentrating the mixture which contains a trans-2,2-dimethyl-3-(hydroxymethyl)cyclopropanecarboxylic acid ester and which is obtained in the above-mentioned step (A).

6. The process according to claim 5, wherein the concentration is conducted after treating the mixture which contains a trans-2,2-dimethyl-3-(hydroxymethyl)cyclopropanecarboxylic acid ester and which is obtained in the above-mentioned step (A), with an acid.

7. The process according to claim 4, wherein the mixture of a trans- and cis-isomers of a 2,2-dimethyl-3-(acyloxymethyl) cyclopropanecarboxylic acid ester is one obtained by reacting a 1-(acyloxy)-3-methyl-2-butene with a diazoacetic acid ester in the presence of a metal catalyst.

8. The process according to claim 7, wherein the reaction of the 1-(acyloxy)-3-methyl-2-butene and the diazoacetic acid ester is conducted under the condition where the amount of water is 0.1% by weight or less per 1 part by weight of the diazoacetic acid ester.

9. The process according to claim 7, wherein the reaction of the 1-(acyloxy)-3-methyl-2-butene and the diazoacetic acid ester is conducted by contacting a composition comprising the 1-(acyloxy)-3-methyl-2-butene and the diazoacetic acid ester with a metal catalyst.

10. The process according to claim 9, wherein the amount of water in the composition comprising the 1-(acyloxy)-3-methyl-2-butene and the diazoacetic acid ester is 0.1% by weight or less per 1 part by weight of the diazoacetic acid ester.

11. The process according to claim 10, wherein the composition comprising the 1-(acyloxy)-3-methyl-2-butene and the diazoacetic acid ester is one obtained by reacting a hydrochloric acid salt of a glycine ester with sodium nitrite in the presence of a 1-(acyloxy)-3-methyl-2-butene and an acid catalyst followed by dehydrating the obtained organic layer.

* * * * *